United States Patent [19]

Signorino et al.

[11] Patent Number: 5,059,248

[45] Date of Patent: Oct. 22, 1991

[54] STABLE, FLUID, AQUEOUS PIGMENT DISPERSIONS FOR USE IN FILM COATING TABLETS AND THE LIKE

[75] Inventors: Charles A. Signorino, King of Prussia, Pa.; Harry Meggos, Godfrey, Ill.

[73] Assignee: Warner-Jenkinson Company, Inc., St. Louis, Mo.

[21] Appl. No.: 392,589

[22] Filed: Aug. 11, 1989

[51] Int. Cl.$^5$ .................... C09B 63/00; C09B 67/02
[52] U.S. Cl. .................... 106/402; 106/400; 106/401; 106/493; 106/499; 106/505; 252/351; 252/352; 252/356; 252/357
[58] Field of Search ............... 106/402, 401, 436, 437, 106/439, 456, 493, 181, 479, 447, 248, 487; 252/356, 357

[56] References Cited

U.S. PATENT DOCUMENTS

| | | | |
|---|---|---|---|
| 3,663,284 | 5/1972 | Stanicoff et al. | 106/447 |
| 3,802,896 | 4/1974 | Westall et al. | 106/248 |
| 3,961,979 | 6/1976 | Abercrombie, Jr. | 106/487 |
| 3,981,984 | 9/1976 | Signorino | 424/33 |
| 4,652,313 | 5/1987 | Den Boer et al. | 106/289 |
| 4,772,331 | 9/1988 | Noguchi et al. | 106/479 |

OTHER PUBLICATIONS

C.A. 88(23): 170454; Hanaki, A.; "Acceleration of the Copper-Catalysed Autooxidation of Cysteine by EDTA and Related Polyaminopolycarboxylic Acids".

Primary Examiner—William R. Dixon, Jr.
Assistant Examiner—Scott L. Hertzog
Attorney, Agent, or Firm—Senniger, Powers, Leavitt & Roedel

[57] ABSTRACT

Improved stable, fluid, aqueous dispersion compositions comprise a pigment, an alkali metal, alkaline earth metal or ammonium salt of a linear aliphatic substituted glycine such as a salt of ethylene diamine tetraacetic acid or nitrilo triacetic acid as a stabilizing agent, and water. The dispersion composition may additionally contain a lower alkanol such as methanol and/or a water soluble plasticizer such as propylene glycol. Coating compositions for use as a film coating for tablets and the like contain the above-described stable, fluid, aqueous dispersion composition, a water soluble plasticizer, a film coating resin, and water. The described fluid, aqueous dispersion compositions have been found to remain stable for extended periods exceeding six months.

32 Claims, No Drawings

STABLE, FLUID, AQUEOUS PIGMENT DISPERSIONS FOR USE IN FILM COATING TABLETS AND THE LIKE

BACKGROUND OF THE INVENTION

This invention relates to pigment dispersions and, more particularly, to stable, fluid, aqueous pigment dispersions for use in film coating tablets and the like.

Suspensions or dispersions of pigments are used for producing coating compositions for film coating pharmaceutical tablets, capsules and the like. The pigments utilized are generally F D & C or D & C lakes or combinations of such lakes with titanium dioxide or iron oxide. The pigment suspension or dispersion is combined with other components (e.g., alcohols, plasticizers and film coating resins) to produce a coating composition used in film coating tablets and the like.

The process of manufacturing food grade lakes terminates in a filter press from which a solid cake is obtained. This filter cake is a stiff material handled as a solid and generally comprises 80% water and 20% lake solids. The possibility of developing a pigment dispersion with lakes in water must overcome the strong attractive forces in the aluminum hydroxide substrate of the lake to tie up large amounts of water in a solid matrix.

It is highly desirable that pigment dispersions or suspensions marketed for use in making film coating compositions have a high concentration of pigment or lake in water (e.g., 25 to 40 wt. %). It is also desirable to provide pigment dispersions or suspensions which are stable and fluid for extended periods of time and in which the pigment particles resist settling.

In the past, efforts have been made to produce pigment dispersions or suspensions having a high concentration of pigment therein. Signorino, U.S. Pat. No. 3,981,984 discloses high concentration pigment suspensions for polymer film coating of tablets and the like which comprise a non-aqueous solvent such as ethanol, pigment particles dispersed in the solvent and an edible protective colloid such as hydroxypropyl cellulose coating the pigment particles. More recently, Den Boer et al., U.S. Pat. No. 4,652,313 describes an aqueous lake pigment suspension comprised of a pigment, a natural or synthetic gum, a salt of a dicarboxylic or tricarboxylic acid compound such as a salt of citric acid or fumaric acid for lowering viscosity, and water. Based upon the data presented, the suspensions disclosed in U.S. Pat. No. 4,652,313 do not appear to provide the desired stability over extended periods of time and empirical data is required to formulate dispersions of various lake pigments with differences in formulations being required for different batches of the same lake.

There is a continuing need, therefore, for fluid, aqueous pigment dispersions which avoid the use of objectionable organic solvents, contain high concentrations of pigment and remain stable and useful for extended periods of time.

SUMMARY OF THE INVENTION

Among the several objects of the invention may be noted the provision of fluid, aqueous pigment dispersions which exhibit improved stability characteristics; the provision of such dispersions which contain high concentrations of pigments; the provision of dispersions of the type indicated which are capable of tolerating the incorporation therein of organic solvents such as methanol without undue thickening of the dispersions; the provision of coating compositions for film coating tablets and the like containing such dispersions; and the provision of coated tablets and the like coated with the use of the novel dispersions of the invention. Other objects will be in part apparent and in part pointed out hereinafter.

Briefly, the present invention is directed to a stable, fluid, aqueous dispersion composition comprising a pigment, a stabilizing agent comprising an alkali metal, alkaline earth metal or ammonium salt of a linear aliphatic substituted glycine, and water. Preferably, the stabilizing agent is an alkali metal, alkaline earth metal or ammonium salt of ethylene diamine tetraacetic acid, nitrilo triacetic acid, diethylene triamine pentaacetic acid, hydroxyethylene diamine triacetic acid, dihydroxyethyl glycine, iminodiacetic acid and ethanol diglycine. The invention is further directed to such stable, fluid, aqueous dispersion compositions which additionally contain a lower alkanol such as methanol and/or a water soluble plasticizer such as propylene glycol. The invention also includes coating compositions for use as a film coating for tablets and the like comprising a stable, fluid, aqueous dispersion composition of the above type, a water soluble plasticizer, a film coating resin, and water, and coated tablets and the like coated with such coating compositions.

DESCRIPTION OF THE PREFERRED EMBODIMENTS

In accordance with the present invention, it has now been found that improved aqueous, fluid and stable dispersions containing high concentrations of pigments can be formulated by utilizing as a stabilizing agent an alkali metal, alkaline earth metal or ammonium salt of a linear aliphatic substituted glycine. Through the use of such a stabilizing agent, fully aqueous dispersions may be formulated which retain their stability, fluidity and usefulness for extended periods of time in excess of about six months and resist settling or lumping.

The stabilizing agents which are useful to impart improved stability characteristics to fluid, aqueous dispersions are the alkali metal, alkaline earth metal and ammonium salts of linear aliphatic substituted glycine compounds. As used herein, the term "linear aliphatic substituted glycine" designates glycine compounds in which the amino group of glycine has been substituted with linear aliphatic groups. Illustrative of the stabilizing agents of this type which may be used in the practice of the invention are the alkali metal (e.g., sodium), alkaline earth metal (e.g., calcium) and ammonium salts of ethylene diamine tetraacetic acid, nitrilo triacetic acid, diethylene triamine pentaacetic acid, hydroxyethylene diamine triacetic acid, dihydroxyethyl glycine, iminodiacetic acid and ethanol diglycine. Similar salts of other linear aliphatic substituted glycine compounds known to the art may also be used. The aforementioned salts of ethylene diamine tetraacetic acid are particularly preferred because of their availability, cost effectiveness and nontoxicity.

Through the use of such stabilizing agents, stable, fluid, aqueous dispersions containing approximately 25 to 40 wt. %, preferably 30 to 35 wt. % of pigment may be prepared, with the stabilizing agent constituting approximately 0.5 to 3.5 wt. %, preferably about 1.5 to 2.5 wt. %, of the pigment in the dispersion compositions. Such aqueous dispersion compositions have been found to retain their stability, i.e., to remain fluid and without settling of the pigment, for periods of at least six months.

The pigment component of the stable, fluid, aqueous dispersion compositions of the invention may be any of the conventionally employed pigments known to the art. Thus, the pigment component may be any FDA approved pigment such as F D & C lakes and D & C lakes (e.g., F D & C Red No. 40, F D & C Red No. 3, F D & C Yellow No. 5, F D & C Yellow No. 6, F D & C Blue No. 1, F D & C Blue No. 2, D & C Yellow No. 7, D & C Blue No. 6, D & C Orange No. 4 and D & C Green No. 5), or carmine. Such F D & C and D & C lakes are commercially available from Warner-Jenkinson Company of St. Louis, Mo. The pigment component may also be constituted by the combination of such lakes or mixture of lakes and titanium dioxide or iron oxide.

The aqueous dispersion compositions of the invention are useful for preparing film coating compositions for film coating tablets and the like for pharmaceutical and food applications, and, advantageously, are compatible with organic solvents such as lower alkanols without causing undue thickening of the dispersion compositions. Thus, alcohols such as methanol, ethanol and isopropanol can be incorporated into the aqueous dispersions of the invention to accelerate evaporation of the liquid portion of the composition in forming coating films without adversely affecting the stability or flowability thereof. It has been found, in this regard, that the aqueous dispersions can tolerate the inclusion of a lower alkanol concentration equal to the pigment concentration without undue effect.

Further, in preparing film coating compositions using the aqueous dispersions of the invention, plasticizers such as propylene glycol, glycerin, polyethylene glycol and others known to the art can be incorporated without adverse effect. In addition, film-forming resins such as methyl cellulose, hydroxypropylmethyl cellulose, hydroxypropyl cellulose, ethyl cellulose, cellulose acetate phthalate, shellac, polyvinyl pyrrolidone or other conventionally employed resins may be included in the aqueous film forming compositions formed from the aqueous dispersions of the invention. Though ethyl cellulose and cellulose acetate phthalate are not water soluble, they are available in water dispersible latex form and may be incorporated in the compositions of the invention. For confectionary and other applications, the aqueous dispersions may also be combined with sugar solutions or syrups for coating solid candy or food forms.

The aqueous dispersions of the invention are stable, uniform, and fluid and retain these desirable properties for extended periods of time without requiring the presence of a gum or other suspending or dispersing aid for stabilization. Moreover, as mentioned, such aqueous dispersions are compatible with organic solvents such as lower alkanol and other components employed in formulating film coating compositions for coating tablets and the like.

The following examples illustrate the practice of the invention:

EXAMPLE 1

A stable, fluid, aqueous dispersion was prepared having the following composition:

| Component | Wt. | Wt. % |
|---|---|---|
| Tetrasodium ethylene diamine tetraacetic acid (38%) | 2 g. | 0.6 |
| TiO$_2$ | 10 g. | 8.3 |
| F D & C Yellow No. 5 (Lake 40%) | 30 g. | 25.0 |
| Distilled H$_2$O | 78 g. | 66.1 |

All of the components were combined in a blender and mixed until a uniform, fluid, aqueous dispersion was formed. The dispersion contained 33.3 wt. % pigment and approximately 0.6 wt. % of the stabilizing agent tetrasodium ethylene diamine tetraacetic acid.

EXAMPLE 2

Example 1 was repeated in preparing a stable, fluid, aqueous dispersion having the following composition:

| Component | Wt. | Wt. % |
|---|---|---|
| Tetrasodium ethylene diamine tetraacetic acid (38%) | 2 g. | 0.6 |
| TiO$_2$ | 10 g. | 8.3 |
| F D & C Yellow No. 5 (Lake 40%) | 30 g. | 25.0 |
| Methyl alcohol | 10 g. | 8.3 |
| Distilled H$_2$O | 68 g. | 56.7 |

The resulting alcohol-water dispersion contained 33.3 wt. % pigment and approximately 0.67 wt. % of the stabilizing agent tetrasodium ethylene diamine tetraacetic acid. The dispersion was still stable and fluid after more than six months.

EXAMPLE 3

Example 1 was repeated in preparing a stable, fluid, coating formulation having the following composition:

| Component | Wt. | Wt. % |
|---|---|---|
| Tetrasodium ethylene diamine tetraacetic acid (38%) | 2 g. | 0.6 |
| TiO$_2$ | 10 g. | 7.5 |
| F D & C Yellow No. 5 (Lake 40%) | 30 g. | 22.5 |
| Propylene glycol | 5 g. | 3.7 |
| Distilled H$_2$O | 86.3 g. | 65.7 |

The resulting composition contained 30 wt. % pigment, approximately 0.6 wt. % of the stabilizing agent tetrasodium ethylene diamine tetraacetic acid, and 3.7 wt. % propylene glycol as a plasticizer. The composition was still stable and fluid after more than six months.

EXAMPLE 4

Example 1 was repeated in preparing a stable, fluid, coating formulation having the following composition:

| Component | Wt. | Wt. % |
|---|---|---|
| Tetrasodium ethylene diamine tetraacetic acid (38%) | 2 g. | 0.6 |
| TiO$_2$ | 10 g. | 7.5 |
| F D & C Yellow No. 5 (Lake 40%) | 30 g. | 22.5 |
| Methyl alcohol | 30 g. | 22.5 |
| Propylene glycol | 5 g. | 3.7 |
| Distilled H$_2$O | 56.3 g. | 43.2 |

The resulting composition contained 30 wt. % pigment, 0.6 wt. % stabilizing agent, 22.5 wt. % methyl alcohol and 3.7 wt. % propylene glycol, and remained stable and fluid after more than six months.

EXAMPLE 5

Example 1 was repeated in preparing a stable, fluid, aqueous dispersion having the following composition:

| Component | Wt. % |
| --- | --- |
| Trisodium nitrilo triacetic acid | 0.6 |
| F D & C Yellow No. 5 (Lake 40%) | 20.0 |
| TiO$_2$ | 10.0 |
| Distilled H$_2$O | 69.4 |

The resulting dispersion remained stable and fluid after more than six months.

EXAMPLE 6

Example 1 was repeated in preparing a stable, fluid, aqueous dispersion having the following composition:

| Component | Wt. % |
| --- | --- |
| Dicalcium ethylene diamine tetraacetic acid | 0.6 |
| F D & C Red No. 40 (Lake 40%) | 20.0 |
| TiO$_2$ | 10.0 |
| Distilled H$_2$O | 69.4 |

The resulting dispersion remained stable and fluid after more than six months.

EXAMPLE 7

Example 1 was repeated in preparing a stable, fluid, aqueous dispersion having the following composition:

| Component | Wt. % |
| --- | --- |
| Tetraammonium ethylene diamine tetraacetic acid | 0.3 |
| F D & C Yellow No. 5 (Lake 40%) | 20.0 |
| TiO$_2$ | 10.0 |
| Distilled H$_2$O | 69.7 |

The resulting dispersion remained stable and fluid after more than six months.

EXAMPLE 8

Example 1 was repeated in preparing a stable, fluid, aqueous dispersion having the following composition:

| Component | Wt. % |
| --- | --- |
| Pentasodium diethylene triamine pentaacetic acid | 0.3 |
| F D & C Yellow No. 5 (Lake 40%) | 20.0 |
| TiO$_2$ | 10.0 |
| Distilled H$_2$O | 69.7 |

The resulting dispersion remained stable and fluid after more than six months.

EXAMPLE 9

A coating composition for use in film coating tablets and the like was prepared by adding 10 g. of the aqueous dispersion of Example 1 to 100 g. of a solution containing 9 g. hydroxypropylmethyl cellulose (Methocel) and 1 g. propylene glycol in water, and stirring vigorously for two minutes with a laboratory mixer. The resulting coating suspension or composition contained 12% solids and was smooth and uniform. This suspension can be sprayed onto solid forms such as tablets in a fluid bed column or in a coating pan adapted for efficient removal of water. The above-described quantity of coating composition would coat 500 g. of tablets in a 4" Wurster column in 12 minutes. The tablets would each have a 2% weight gain and would be uniformly colored by the incorporation of the dispersion of Example 1 in the film applied.

EXAMPLE 10

The following procedure was used in film coating pistachio nuts with an aqueous dispersion of the invention.

A stable, fluid, aqueous dispersion was prepared having the following composition:

| Component | Wt. % |
| --- | --- |
| Tetrasodium ethylene diamine tetraacetic acid | 1.50 |
| F D & C Red No. 40 (Lake 40%) | 31.50 |
| TiO$_2$ | 2.50 |
| Distilled H$_2$O | 64.50 |
| | 100.00 |

An aqueous film coating polymer solution was prepared having the following composition:

| Component | Wt. % |
| --- | --- |
| Hydroxypropylmethyl cellulose (Methocel E-15) | 5.00 |
| Hydroxypropylmethyl cellulose (Methocel E-5) | 5.00 |
| Propylene glycol | 1.00 |
| Distilled H$_2$O | 89.00 |
| | 100.00 |

A film coating suspension was prepared by adding 13 g. of the above-noted aqueous dispersion to 115 g. of the above-described aqueous polymer solution. The resulting suspension contains approximately 16% solids.

The suspension was sprayed onto 400 g. of pistachio nuts in a 4" Wurster column. The theoretical weight gain for each nut was 4%, and the coating sprayed onto the nuts produced a smooth, uniform coating.

EXAMPLE 11

The aqueous dispersion described in Example 10 was used in a sugar syrup system for coating tablets. The sugar base coating syrup contained 70% sugar and 30% water. 92.65 parts by weight of the sugar syrup and 7.35 parts by weight of the aqueous dispersion were combined to form a coating composition. The composition was used to pan coat placebo tablets and produced a smooth, even coat on the tablets.

In view of the above, it will be seen that the several objects of the invention are achieved and other advantageous results attained.

As various changes could be made in the above compositions without departing from the scope of the invention, it is intended that all matter contained in the above description or shown in the accompanying drawings shall be interpreted as illustrative and not in a limiting sense.

What is claimed is:

1. A stable, fluid, aqueous dispersion composition consisting essentially of from approximately 25 to 40 wt. % of a pigment selected from the group consisting of an FD&C lake, a D&C lake and ceramine or a combination of such lakes with titanium dioxide or iron oxide, a stabilizing agent selected from the group consisting of an alkali metal, alkaline earth metal or ammonium salt of a linear aliphatic substituted glycine, said stabilizing agent constituting from approximately 0.5 to 3.5 wt. % of said pigment, and water.

2. A stable, fluid, aqueous dispersion composition as set forth in claim 1 wherein said stabilizing agent is selected from the group consisting of the alkali metal, alkaline earth metal and ammonium salts of ethylene diamine tetraacetic acid, nitrilo triacetic acid, diethylene triamine pentaacetic acid, hydroxyethylene diamine triacetic acid, dihydroxyethyl glycine, iminodiacetic acid and ethanol diglycine.

3. A stable, fluid, aqueous dispersion composition as set forth in claim 2 wherein said stabilizing agent is the disodium salt of ethylene diamine tetraacetic acid.

4. A stable, fluid, aqueous dispersion composition as set forth in claim 2 wherein said stabilizing agent is the tetrasodium salt of ethylene diamine tetraacetic acid.

5. A stable, fluid, aqueous dispersion composition as set forth in claim 2 wherein said stabilizing agent is the calcium disodium salt of ethylene diamine tetraacetic acid.

6. A stable, fluid, aqueous dispersion composition as set forth in claim 2 wherein said stabilizing agent is the trisodium salt of nitrilo triaacetic acid.

7. A stable, fluid, aqueous dispersion composition as set forth in claim 2 wherein said stabilizing agent is the pentasodium salt of diethylene triamine pentaacetic acid.

8. A stable, fluid, aqueous dispersion composition as set forth in claim 2 wherein said stabilizing agent is the disodium salt of ethanol diglycine.

9. A stable, fluid, aqueous dispersion composition as set forth in claim 2 wherein said stabilizing agent is the disodium salt of imino diacetic acid.

10. A stable, fluid, aqueous dispersion composition as set forth in claim 1 wherein said pigment is a combination of an FD&C lake or a D&C lake and titanium dioxide or iron oxide.

11. A stable, fluid, aqueous dispersion composition as set forth in claim 1 wherein said stabilizing agent constitutes approximately 1.5 to 2.5 wt. % of said pigment in the composition.

12. A stable, fluid, aqueous dispersion composition consisting essentially of from approximately 25 to 40 wt. % of a pigment selected from the group consisting of an FD&C lake, a D&C lake and carmine or a combination of one of such lakes with titanium dioxide or iron oxide, a stabilizing agent selected from the group consisting of an alkali metal, alkaline earth metal or ammonium salt of ethylene diamine tetraacetic acid, diethylene triamine pentaacetic acid and dihydroxyethyl glycine, said stabilizing agent constituting from approximately 0.5 to 3.5 wt. % of said pigment, from approximately 25 to 40% wt. % of a lower alkanol and water.

13. A stable, fluid, aqueous dispersion composition as set forth in claim 12 wherein said lower alkanol is methanol.

14. A stable, fluid, aqueous dispersion composition as set forth in claim 12 wherein said lower alkanol is ethanol.

15. A stable, fluid, aqueous dispersion composition as set forth in claim 12 wherein said stabilizing agent is the disodium salt of ethylene diamine tetraacetic acid.

16. A stable, fluid, aqueous dispersion composition as set forth in claim 12 wherein said stabilizing agent is the tetrasodium salt of ethylene diamine tetraacetic acid.

17. A stable, fluid, aqueous dispersion composition as set forth in claim 12 wherein said stabilizing agent is the calcium disodium salt of ethylene diamine tetraacetic acid.

18. A stable, fluid, aqueous dispersion composition as set forth in claim 15 wherein said pigment is a combination of an FD&C lake or a D&C lake and titanium dioxide or iron oxide.

19. A stable, fluid, aqueous dispersion composition comprising the stable, fluid, aqueous dispersion of claim 15 and a water soluble plasticizer.

20. A stable, fluid, aqueous dispersion composition as set forth in claim 19 wherein said water soluble plasticizer is selected from the group consisting of glycerin, propylene glycol and polyethylene glycol.

21. A coating composition for use as a film coating for tablets comprising the stable, fluid, aqueous dispersion of claim 1, a water soluble plasticizer, a film coating resin, and water.

22. A coating composition as set forth in claim 21 wherein said film coating resin is selected from the group consisting of methyl cellulose, hydroxypropylmethyl cellulose, hydroxypropyl cellulose, ethyl cellulose, cellulose acetate phthalate, shellac and polyvinyl pyrrolidone.

23. A coating composition as set forth in claim 21 wherein said film coating resin is hydroxypropylmethyl cellulose.

24. A coating composition as set forth in claim 21 wherein said water soluble plasticizer is selected from the group consisting of glycerin, propylene glycol and polyethylene glycol.

25. A coated tablet having as the coating a thin film comprising the stable, fluid, aqueous dispersion of claim 1, a water soluble plasticizer, a film coating resin, and water.

26. A coated tablet as set forth in claim 25 wherein said film coating resin is hydroxypropylmethyl cellulose.

27. A coated tablet as set forth in claim 25 wherein the stabilizing agent in said stable, fluid, aqueous dispersion is the disodium salt of ethylene diamine tetraacetic acid.

28. A coated tablet as set forth in claim 25 wherein the stabilizing agent in said stable, fluid, aqueous dispersion is the tetrasodium salt of ethylene diamine tetraacetic acid.

29. A coated tablet as set forth in claim 25 wherein the stabilizing agent in said stable, fluid, aqueous dispersion is the calcium disodium salt of ethylene diamine tetraacetic acid.

30. A coated tablet as set forth in claim 25 wherein the pigment in said stable, fluid, aqueous dispersion is an F D & C lake, D & C lake or carmine or mixtures thereof.

31. A coated tablet as set forth in claim 25 wherein the stabilizing agent in said stable, fluid, aqueous dispersion constitutes from approximately 0.5 to 3.5 wt. % of the pigment in said dispersion.

32. A coated tablet as set forth in claim 25 wherein the pigment in said stable, fluid, aqueous dispersion constitutes approximately 25 to 40 wt. % of said dispersion.

* * * * *

UNITED STATES PATENT AND TRADEMARK OFFICE
CERTIFICATE OF CORRECTION

PATENT NO. : 5,059,248

DATED : October 22, 1991

INVENTOR(S) : Charles A. Signorino & Harry Meggos

It is certified that error appears in the above-identified patent and that said Letters Patent is hereby corrected as shown below:

Column 7, claim 1, line 2, "ceramine" should read ---carmine---.

Signed and Sealed this

Thirtieth Day of March, 1993

Attest:

STEPHEN G. KUNIN

Attesting Officer

Acting Commissioner of Patents and Trademarks